United States Patent [19]

Besmar et al.

[11] Patent Number: 4,720,592

[45] Date of Patent: Jan. 19, 1988

[54] PREPARATION OF CYCLOHEXANONE AND CYCLOHEXANOL

[75] Inventors: Usamah N. Besmar, Houston; John B. Lyon, Orange; Francis J. Miller, Orange; Michael T. Musser, Orange, all of Tex.

[73] Assignee: E. I. Du Pont de Nemours and Company, Wilmington, Del.

[21] Appl. No.: 904,006

[22] Filed: Sep. 5, 1986

[51] Int. Cl.$^4$ ............................................. C07C 29/132
[52] U.S. Cl. ...................................... 568/342; 568/835; 568/836
[58] Field of Search ....................... 568/342, 835, 836

[56] References Cited

U.S. PATENT DOCUMENTS

| | | | |
|---|---|---|---|
| 3,530,185 | 9/1970 | Pugi | 568/342 |
| 3,694,511 | 9/1972 | Nouvel | 568/342 |
| 3,923,895 | 12/1975 | Costantini et al. | 568/836 |
| 3,927,108 | 12/1975 | van de Moesdijk et al. | 568/342 |
| 3,957,876 | 5/1976 | Rapaport et al. | 568/342 |
| 4,115,207 | 9/1978 | Murtho | 568/342 |

OTHER PUBLICATIONS

Tozawa et al., Chem. Abst., vol. 101, #41619f (1984).
Nishimura et al., Chem. Abst., vol. 85, #195951w (1976).
F. Pat. 2,308,596, Chem. Abst., vol. 87, #50353f (1977).

*Primary Examiner*—James H. Reamer

[57] ABSTRACT

The reaction mixture obtained by oxidation of cyclohexane using a cobalt catalyst is extracted with water to remove undesirable oxidation products such as diacids, hydroxy acids, and cobalt catalyst. The resulting mixture is then hydrogenated using a fixed bed hydrogenation catalyst to convert cyclohexyl hydroperoxide to cyclohexanol and cyclohexanone.

8 Claims, 1 Drawing Figure

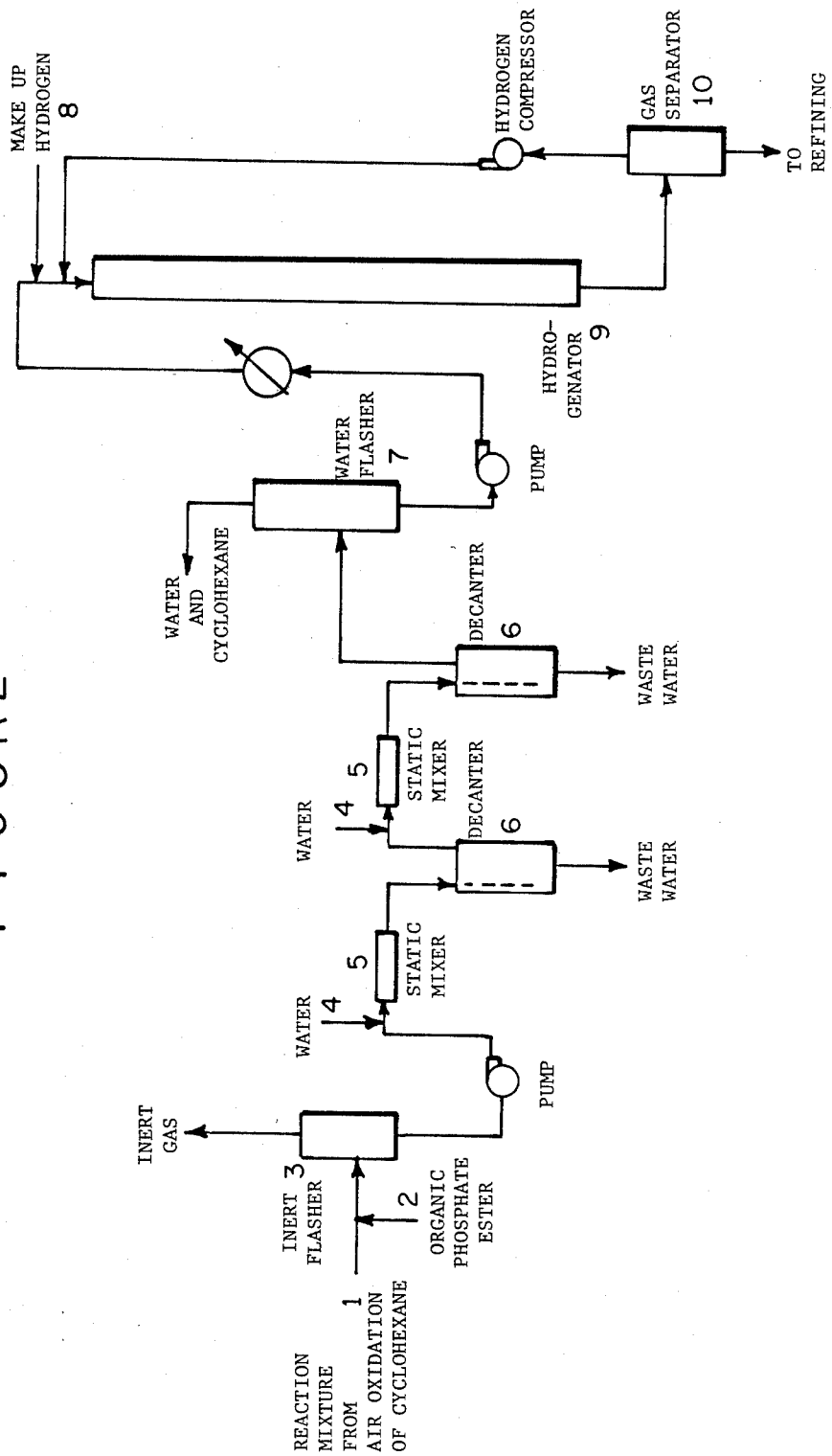
FIGURE

PREPARATION OF CYCLOHEXANONE AND CYCLOHEXANOL

FIELD OF THE INVENTION

The present invention is a process for the preparation of cyclohexanone and cyclohexanol from a mixture containing cyclohexyl hydroperoxide. The process produces the desired products in high yield, for extended periods without reactor fouling, from a feed stream containing cobalt catalyst that was employed in the preparation of the cyclohexyl hydroperoxide from cyclohexane.

BACKGROUND INFORMATION

The preparation of a mixture containing cyclohexanol, cyclohexanone and cyclohexyl hydroperoxide by the air oxidation of cyclohexane with cobalt catalysts is described in Pugi U.S. Pat. No. 3,530,185 and Rapoport U.S. Pat. No. 3,957,867.

The preparation of cyclohexanone and cyclohexanol from cyclohexyl hydroperoxide by hydrogenation using as catalyst a group VIII metal deposited on an inert support is described in Nouvel U.S. Pat. No. 3,694,511.

The preparation of cyclohexanone and cyclohexanol from cyclohexyl hydroperoxide by hydrogenation using a finely divided Group VIII metal that is suspended in the reaction medium is disclosed in van de Moesdijk U.S. Pat. No. 3,927,108. In Example VI this patent shows water-washing the product of the air oxidation of cyclohexane prior to hydrogenation of the cyclohexyl hydroperoxide.

Constantini, et al U.S. Pat. No. 3,923,895 discloses a process for hydrogenation of a water-washed mixture containing cyclohexyl hydroperoxide, to form cyclohexanone and cyclohexanol using a chromium catalyst and a mono or diester of orthophosphoric acid.

It is known from Sipos European Patent Application 0063931, to carry out the air oxidation of cyclohexane using a binary catalyst system of cobalt and chromium compounds and free dialkyl phosphate.

When a mixture containing cyclohexyl hydroperoxide and cobalt catalyst is formed, for example, during the air oxidation of cyclohexane as disclosed, for example, by Pugi, the cyclohexyl hydroperoxide will react catalytically with the cobalt catalyst to form a mixture of products including cyclohexanone and cyclohexanol, but the reaction does not produce these products in high yield, and other waste products are also formed.

If a mixture containing cyclohexyl hydroperoxide and a cobalt catalyst is subjected to a hydrogenation reaction in the presence of a fixed bed hydrogenation catalyst, cyclohexanone and cyclohexanol are among the products produced, but the reactor soon becomes fouled with cobalt containing residues and with residues from other oxidation products produced during the initial oxidation reaction, i.e., diacids and hydroxy acids, and the reaction slows and the yield of desired product is reduced.

SUMMARY OF THE INVENTION

The present invention is a process for producing cyclohexanone and cyclohexanol from a mixture containing cyclohexane, a cyclohexane oxidation cobalt catalyst which is cyclohexane soluble, an organic phosphate ester which is soluble in the mixture, cyclohexanone, cyclohexanol, cyclohexyl hydroperoxide, and other oxidation products of the oxidation of cyclohexane including diacids, monoacid and hydroxyacids. Such a mixture may be obtained by the air oxidation of cyclohexane using a cobalt catalyst in a tower oxidizer, in which organic phosphate ester is added at various stages in the tower, or such a mixture may be obtained by the addition of the organic phosphate ester to the mixture obtained after completion of a tower oxidation process or from other sources.

The above mixture is extracted with water to remove a substantial portion of the other oxidation product, especially the diacids and the hydroxy acids. It is these other oxidation products that are the major cause of fouling in the subsequent hydrogenation step. The extraction also removes much of the cobalt catalyst. The removal of much of the cobalt catalyst is beneficial in that if cobalt catalyst is present at high concentration in the hydrogenation step it causes the peroxide to react in such a way that the yield of the desired products is reduced. The water extraction can remove up to about 75% of the other oxidation products, and up to about 90% of the cobalt catalyst. The remaining components are then subjected to hydrogenation over a fixed bed catalyst.

The apparatus shown in the FIGURE is a schematic illustration of the equipment arrangement that may be employed to carry out the process of the invention.

DETAILED DESCRIPTION OF THE INVENTION

The process of the invention is usually carried out on the reaction mixture obtained from the air oxidation of cyclohexane in which a cobalt catalyst soluble in the cyclohexane is employed. See 1 on the drawing. Catalysts of this type are disclosed in Rapoport, et al U.S. Pat. No. 3,957,876, and include cobalt napthenate, cobalt octoate, cobalt laurate, cobalt palminate, cobalt stearate, cobalt linoleate, cobalt acetylacetonate and mixtures thereof. Such a reaction mixture contains a high proportion (usually over 90%) of unreacted cyclohexane and up to 10 percent by weight of oxidation products including cyclohexanol, cyclohexanone, cyclohexylhydroperoxide and other oxidation products. About 1 to 3% by weight of the reaction mixture is other oxidation products including diacids, monoacids and hydroxy acids. Diacids and hydroxy acids are usually about 50 to 65% by weight of the other oxidation products.

Organic phosphate ester may be present during the oxidation reaction. If present during oxidation, the organic phosphate ester tends to reduce or eliminate fouling of the oxidizer equipment. Alternatively, the organic phosphate ester may be added to the oxidized mixture obtained on the passage of the mixture from the oxidizer, as shown at 2 on the drawing. It is, of course, possible to add phosphate ester during the course of the oxidation reaction, and add more phosphate ester after the oxidization reaction is complete. The amount of organic phosphate ester present in the mixture prior to water extraction should exceed on a molar basis the amount of cobalt present in the mixture, and preferably the molar ratio of organic phosphate to cobalt is in the range of 3:1 to 50:1.

Suitable organic phosphate esters have the formula:

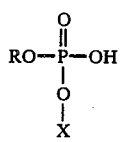

where R is selected from the group consisting of $C_4$–$C_{12}$ alkyl radicals and $C_5$–$C_8$ cycloalkyl radicals, and X is H or R. A commercially available organic phosphate ester that is suitable is sold under the name Emphos PS-400, and it contains 7.4 mol % phosphoric acid, 57.4 mol % mono(2-ethylhexyl)phosphoric acid and 35.2 mol % di(2-ethylhexyl)phosphoric acid.

The mixture containing the organic phosphate ester is then passed through a zone of reduced pressure, an inert flasher 3, where inert gas, mostly nitrogen, is removed.

The mixture is then extracted with water, for example, by adding water 4, and passing the mixture through a series of static mixers 5 and decanters 6, which removes a substantial portion of the other oxidation products present, i.e., diacids, monoacids and hydroxyacids. Alternatively, a single fixed bed countercurrent extractor may be employed. Preferably more than 50% of the other oxidation products are removed, and often up to about 75% of the other oxidation products are removed. The other oxidation products include: 6-hydroxyl caproic acid, 5-hydroxy valeric acid, succinic acid, adipic acid, and formic acid. The extraction also removes much of the cobalt catalyst. More than 50% of the cobalt catalyst is often removed in the water extraction step, and as much as a 90% extraction is occasionally achieved.

Water is slightly soluble in the mixture to be extracted. The amount of water employed in the extraction step must therefore exceed the amount soluble in the mixture to be extracted. Although some increase in the amount of other oxidation products and cobalt catalyst removed is achieved if more than 10 volume % water is employed, sufficient quantities are removed if between 2 and 10 volume % water is used, and usually between 2 and 6% water is sufficient.

After extraction it is preferred to remove the water that has dissolved in the mixture by flashing it off—that is, by reducing the pressure on the mixture in, for example, a water flasher 7, which also removes a portion of the cyclohexane in the stream.

The mixture is then passed to a hydrogenator filled with catalyst. Suitable hydrogenation catalyst are Group VIII metals on inert substrates, such as platinum, ruthenium or palladium on carbon, alumina, silica, or titanium dioxide. The metals should be present in the amount of about 0.1 to 1% of the weight of the catalyst. Mixtures of Group VIII metals may be employed. Hydrogen 8 is fed into the feed stream. Unreacted hydrogen may be separated from the hydrogenated mixture by a gas separator 10, and the hydrogen recycled to the hydrogenator.

EXAMPLE I

Cyclohexane was oxidized in the liquid phase with air, in the presence of cobalt octoate catalyst at a pressure of about 170 psi. The cobalt content of the stream was about 0.1 ppm. Two of the components of the "other oxidation products" were measured: the stream contained about 0.13 weight % adipic acid and about 0.26 wt percent 6-hydroxy caproic acid. A commercial alkyl phosphate (Emphos PS-400) was injected into the oxidizer tails at 6 ppm concentration. The mixture was extracted with water, 2.5% by volume, at 127° C. in two mixer/separator stages and then flashed to remove water. The resulting mixture contained cyclohexane, 1.212 weight % cyclohexylhydroperoxide, 0.087 weight % dicyclohexylperoxide, 0.029 weight % 2-cyclohexyl-2-methylfuranylperoxide, 0.886 weight % cyclohexanone, 2.32 weight % cyclohexanol, 128 ppm cyclohexenone and about 0.02 ppm cobalt. Analysis showed that between about 65 and 85 weight % of the adipic acid and 6-hydroxy caproic acid were extracted. This mixture was hydrogenated at 150° C. and 165 psia in a 6-inch×9-foot long fixed bed containing 60 pounds of 1/12-inch spheres of 0.5% palladium on silica catalyst. After 62 days of operation (56,000 pounds of feed per pound of catalyst), the hydrogenation rate remained high for cyclohexylhydroperoxide (99%), 2-cyclohexyl-2-methylfuranylperoxide (81%), cyclohexenone (98%), and dicyclohexylperoxide (60%). The ratio of cyclohexanol to cyclohexanone produced across the hydrogenator remained high at 5.5. A high percentage of peroxide exiting the air oxidizer (>80%) reached the hydrogenator. The yield of cyclohexanol and cyclohexanone was 92% based on converted peroxide. The moles of hydrogen consumed per mole of peroxide consumed was 0.60, with the remaining hydrogen dissolved in the hydrogenator tails stream. The catalyst removed at the end of the run was clean and free flowing.

EXAMPLE II

Example I was repeated. After 3 days of continuous operation, injection of the Emphos PS-400 was stopped. As a result, conversion of the dicyclohexylperoxide across the hydrogenator dropped from 60% to zero, and cyclohexenone conversion, a measure of hydrogenation activity, dropped from 96% to 85%. Conversion of both dicyclohexylperoxide and cyclohexenone recovered completely after Emphos injection was resumed.

CONTROL EXAMPLE I

Example I was repeated except the oxidation mixture was not extracted with water before the fixed bed hydrogenator. The 0.5% palladium on silica catalyst removed after 800 hours of operation was uniformly coated with a grayish powder of primarily cobalt phosphate. The ratio of cyclohexanol to cyclohexanone produced steadily dropped from 5.5 to 3.3 at the end of the run, indicating a decrease in the fraction of peroxide being hydrogenated.

CONTROL EXAMPLE II

By oxidation of cyclohexane in the liquid phase with air, in the presence of cobalt octoate catalyst, and subsequent flashing and filtration, an oxidation mixture was prepared and then hydrogenated in a packed bed of 0.5% palladium on silica catalyst. The catalyst was gradually deactivated and the ratio of cyclohexanol to cyclohexanone produced declined steadily from 5 to 2. The catalyst removed after 25 days of operation was fused with organic foulant that made the catalyst removal from the reactor extremely difficult.

We claim:
1. A process for the production of a mixture containing cyclohexanone and cyclohexanol which comprises the following steps in sequence:

(A) contacting a mixture containing (i) cyclohexane, (ii) a cyclohexane oxidation cobalt catalyst which is soluble in cyclohexane, (iii) an organic phosphate ester which is soluble in the mixture and having the formula:

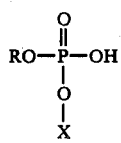

where R is selected from the group consisting of $C_4$–$C_{12}$ alkyl radicals and $C_5$–$C_8$ cycloalkyl radicals, and X is H or R, (iv) cyclohexylhydroperoxide, cyclohexanol, cyclohexanone, and other oxidation products of the oxidation of cyclohexane including diacids, monoacids and hydroxyacids, the amount of organic phosphate ester in said mixture exceeding the amount, on a molar basis, of cobalt in said mixture, with water under conditions such that the water extracts from the mixture a substantial portion of the cobalt catalyst, (B) separating the water containing the extracted components from the remaining components of the mixture by decantation, (C) contacting the remaining components of the mixture with a fixed bed Group VIII metal on an inert substrate hydrogenation catalyst and hydrogenating the cyclohexylhydroperoxide in the mixture at an elevated temperature and at a pressure of 140–170 psig, to form cyclohexanone and cyclohexanol.

2. The process of claim 1 in which the cobalt catalyst is selected from the group consisting of cobalt naphthenate, cobalt octoate, cobalt laurate, cobalt palminate, cobalt stearate, cobalt linoleate, cobalt acetylacetonate and mixtures thereof.

3. The process of claim 1 in which step (C) is carried out at temperatures in the range of 130°–150° C. at a pressure of 140–170 psig.

4. The process of claim 2 in which the amount of organic phosphate ester in the mixture extracted with water, is on a molar basis, present in a ratio to cobalt of 3:1 to 50:1.

5. The process of claim 1 in which the catalyst of step (C) is palladium on silica.

6. The process of claim 1 in which more than 50% of the other oxidation products are extracted by the water.

7. The process of claim 1 in which more than 50% of the cobalt catalyst is extracted by the water.

8. The process of claim 5 in which the palladium on silica catalyst contains 0.1 to 1% palladium.

* * * * *